United States Patent
Rudie et al.

[11] Patent Number: 6,161,049
[45] Date of Patent: Dec. 12, 2000

[54] THERMAL THERAPY CATHETER

[75] Inventors: Eric N. Rudie; Scott Stockmoe, both of Maple Grove; Aaron Hjelle, Coon Rapids; Bruce W. Ebner, Excelsior; Joel Crabb, Minneapolis, all of Minn.

[73] Assignee: Urologix, Inc., Minneapolis, Minn.

[21] Appl. No.: 09/303,259

[22] Filed: Apr. 30, 1999

Related U.S. Application Data

[60] Provisional application No. 60/126,330, Mar. 26, 1999, abandoned.

[51] Int. Cl.7 ........................................................ A61F 2/00
[52] U.S. Cl. ............................ 607/101; 607/102; 607/105
[58] Field of Search .............................. 607/96, 101, 102, 607/104, 105, 113; 606/28, 29, 31

[56] References Cited

U.S. PATENT DOCUMENTS

| | | |
|---|---|---|
| 4,342,316 | 8/1982 | Rosenberg . |
| 4,406,656 | 9/1983 | Hattler et al. . |
| 4,662,383 | 5/1987 | Sogawa et al. . |
| 4,676,258 | 6/1987 | Inokuchi et al. . |
| 4,878,495 | 11/1989 | Grayzel . |
| 4,887,614 | 12/1989 | Shirakami et al. . |
| 4,983,165 | 1/1991 | Loiterman . |
| 5,007,437 | 4/1991 | Sterzer . |
| 5,015,231 | 5/1991 | Keith et al. . |
| 5,108,370 | 4/1992 | Walinsky . |
| 5,195,965 | 3/1993 | Shantha ...................... 604/54 |
| 5,226,887 | 7/1993 | Farr et al. . |
| 5,304,214 | 4/1994 | DeFord et al. . |
| 5,308,323 | 5/1994 | Sogawa et al. . |
| 5,308,356 | 5/1994 | Blackshear, Jr. et al. . |
| 5,350,361 | 9/1994 | Tsukashima et al. . |
| 5,383,856 | 1/1995 | Bersin . |
| 5,496,271 | 3/1996 | Burton et al. . |
| 5,501,667 | 3/1996 | Verduin, Jr. . |
| 5,505,702 | 4/1996 | Arney . |
| 5,549,559 | 8/1996 | Eshel . |
| 5,645,529 | 7/1997 | Fagan et al. . |
| 5,800,486 | 9/1998 | Thome et al. ........................... 607/105 |
| 5,899,932 | 5/1999 | Dann et al. ............................. 607/113 |

FOREIGN PATENT DOCUMENTS

4-28377  1/1992  Japan .

*Primary Examiner*—Linda C. M. Dvorak
*Assistant Examiner*—Roy Gibson
*Attorney, Agent, or Firm*—Kinney & Lange, P.A.

[57] ABSTRACT

A thermal therapy catheter includes a catheter shaft having an outer surface that is insertable into the body lumen. The catheter shaft carries an energy-emitting element. A multi-lobe balloon is positioned around the outer surface of the catheter shaft adjacent to the energy-emitting element, with opposing ends of the multi-lobe balloon being sealingly connected to the catheter shaft to form a chamber between the multi-lobe balloon and the outer surface of the catheter shaft. A fluid is circulated between the outer surface of the catheter shaft and the multi-lobe balloon in a defined fluid flow path to firmly contact the wall of the body lumen and thereby conductively cool the body lumen tissue while thermally treating targeted tissue at a depth from the body lumen wall.

12 Claims, 5 Drawing Sheets

THERMAL THERAPY CATHETER

CROSS-REFERENCE TO RELATED APPLICATION(S)

This application claims priority from Provisional Application Ser. No. 60/126,330 filed Mar. 26, 1999, now abandoned, for "Thin-Walled Catheter Having Defined Fluid Flow Path" by E. Rudie, S. Stockmoe and A. Hjelle.

BACKGROUND OF THE INVENTION

The present invention relates to a thermal treatment catheter, and more particularly to a catheter having a thin outer wall and a defined fluid flow path within the outer wall to improve the effects of conductive cooling of the wall of the body conduit in which the catheter is inserted.

The prostate gland is a complex, chestnut-shaped organ which encircles the urethra immediately below the bladder. Nearly one third of the prostate tissue anterior to the urethra consists of fibromuscular tissue that is anatomically and functionally related to the urethra and the bladder. The remaining two thirds of the prostate is generally posterior to the urethra and is comprised of glandular tissue. The portion of the urethra extending through the prostate (i.e., the prostatic urethra) includes a proximal segment, which communicates with the bladder, and a distal segment, which extends at an angle relative to the proximal segment by the verumontanum.

Although a relatively small organ, the prostate is the most frequently diseased of all internal organs and is often the site of a common affliction among older men, benign prostatic hyperplasia (BPH), as well as a more serious affliction, cancer. BPH is a nonmalignant, bilateral expansion of prostate tissue occurring mainly in the transition zone of the prostate adjacent to the proximal segment of the prostatic urethra. As this tissue grows in volume, it encroaches on the urethra extending into the region of the bladder neck at the base of the bladder. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Benign prostatic hyperplasia (BPH) may be treated using transurethral thermal therapy as described in further detail in U.S. Pat. No. 5,413,588 entitled DEVICE AND METHOD FOR ASYMMETRICAL THERMAL THERAPY WITH HELICAL DIPOLE MICROWAVE ANTENNA and in U.S. Pat. No. 5,575,811 entitled BENIGN PROSTATIC HYPERPLASIA TREATMENT CATHETER WITH URETHRAL COOLING, both of which are hereby incorporated by reference. During transurethral thermal therapy, the transition zone of the prostate is heated to necrose the tumorous tissue that encroaches on the urethra. Transurethral thermal therapy is administered by use of a microwave antenna-containing catheter which includes a multi-lumen shaft. The catheter is positioned in the urethra with the microwave antenna located adjacent to the hyperplastic prostatic tissue. Energization of the microwave antenna causes the antenna to emit electromagnetic energy which heats tissue within the prostate. A cooling fluid is circulated through the catheter to preserve tissue such as the urethral wall between the microwave antenna and the target tissue of the prostate.

The commercially available Targis™ system from Urologix, Inc. of Minneapolis, Minn. employs a thermal therapy catheter that embodies the aforementioned U.S. Pat. No. 5,413,588, and is a product capable of performing thermal therapy of the prostate with microwave energy delivered from an applicator positioned in the urethra. The Targis™ system has achieved substantial clinical and commercial success, indicating the efficacy of microwave thermal therapy for treating prostate disease. Therefore, there is a continuing need for further developments in the technology of thermal therapy catheters to enhance the effects of microwave treatment of the prostate. In particular, a catheter design exhibiting improved urethral cooling and having decreased manufacturing cost, as well as several other desirable features, would further advance the state of the art.

BRIEF SUMMARY OF THE INVENTION

The present invention is a device and method for treating tissue adjacent to a body lumen such as a urethra. A catheter shaft having an outer surface is insertable into the body lumen, and the catheter shaft carries an energy-emitting element. A multi-lobe balloon is positioned around the outer surface of the catheter shaft adjacent to the energy-emitting element, with opposing ends of the multi-lobe balloon being sealingly connected to the catheter shaft to form a chamber between the multi-lobe balloon and the outer surface of the catheter shaft. A fluid is circulated between the outer surface of the catheter shaft and the multi-lobe balloon in a defined fluid flow path to firmly contact the wall of the body lumen and thereby conductively cool the body lumen tissue while thermally treating targeted tissue at a depth from the body lumen wall.

DETAILED DESCRIPTION

Figure 1:
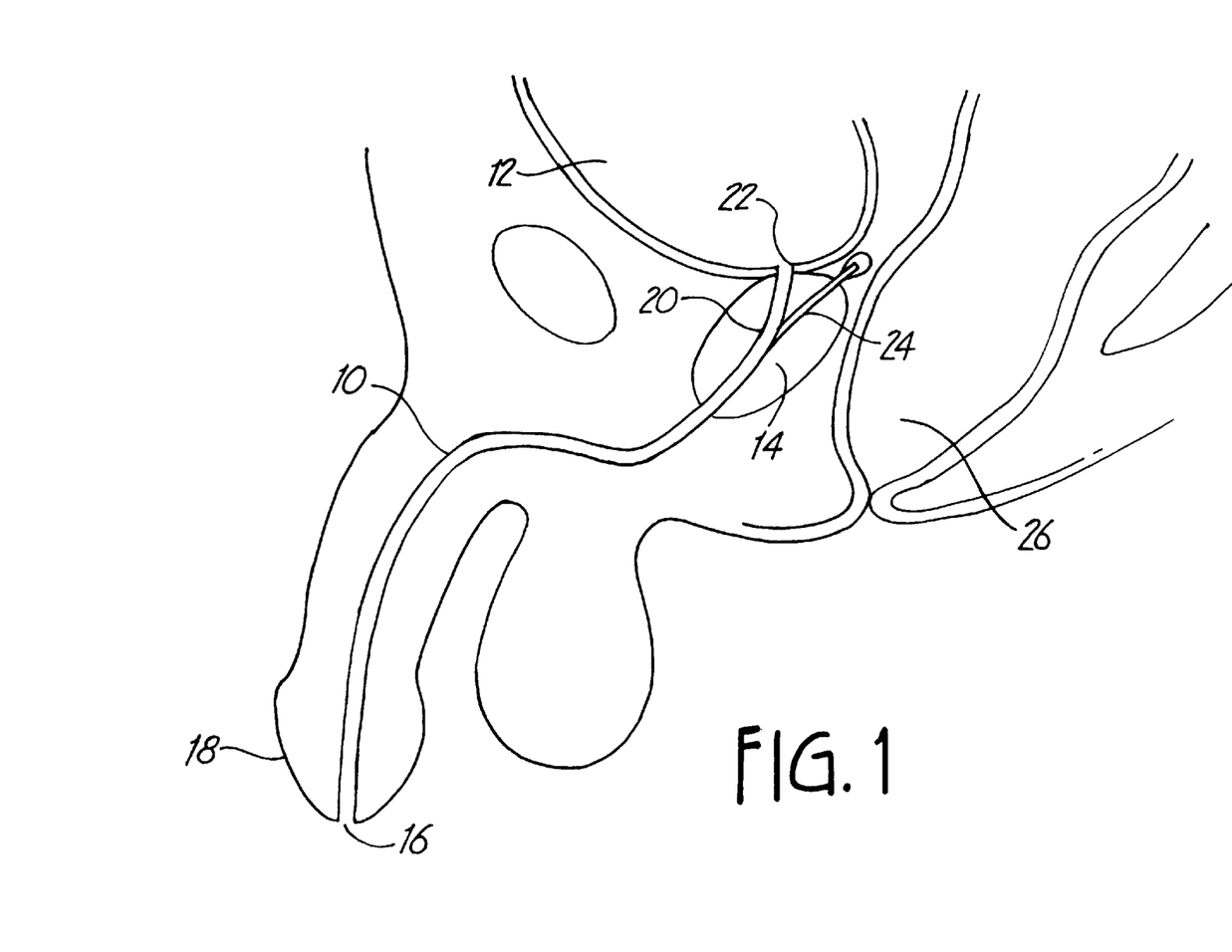
FIG. 1 is a vertical sectional view of a male pelvic region showing the urinary organs affected by benign prostatic hyperplasia.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, a selected volume of tissue of prostate 14 can be necrosed while preserving the tissue of urethra 10 and adjacent tissue such as ejaculatory duct 24 and rectum 26. This is achieved by microwave antenna-containing catheter 28 of the present invention, which is shown in FIGS. 2–6.

Figure 2:
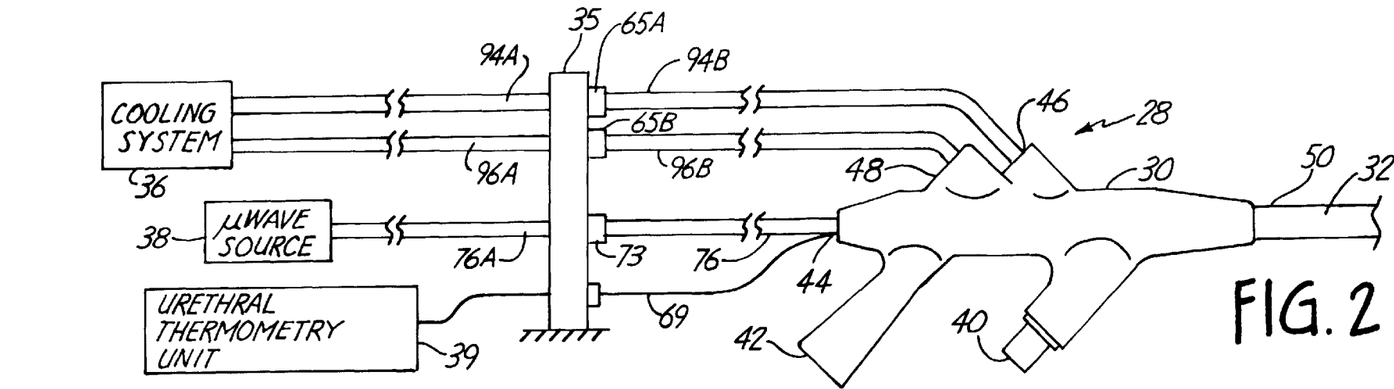
FIG. 2 is a side view of the distal end of the thermal therapy catheter of the present invention.

FIG. 2 shows a side view of a distal end of catheter 28. Catheter 28 generally includes multi-port handle 30, multi-lumen shaft 32, shaft position retention balloon 34 (FIG. 3), connection manifold 35, cooling system 36, microwave generating source 38 and thermometry unit 39. Multi-port handle 30 includes inflation port 40, urine drainage port 42, microwave antenna port 44, cooling fluid intake port 46 and cooling fluid exit port 48. Ports 40–48 communicate with corresponding lumens within shaft 32. Handle 30 is preferably constructed as a two-piece snap-fit shell, composed of a thermoplastic elastomer ora similar material, with appropriate ports and channels being formed therein for communication with the lumens utilized by the thermal therapy catheter of the present invention.

Figure 5:
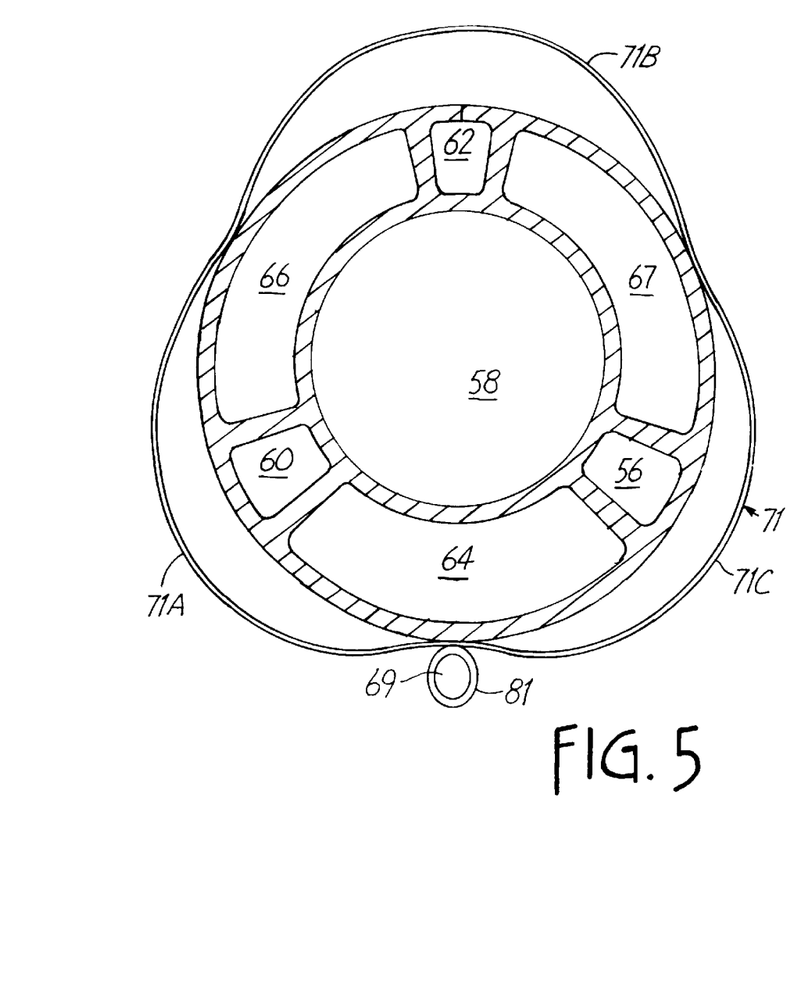
FIG. 5 is a section view of the thermal therapy catheter of the present invention, taken along line 5—5 of FIG. 4.

Shaft 32 is connected to handle 30 at shaft distal end 50. Shaft 32 is a multi-lumen, Foley-type urethral catheter shaft which is preferably extruded from a flexible thermoplastic elastomer. Shaft 32, which has an outer diameter of about 18 French, includes outer surface 52, which is generally circular in cross-section as shown in FIG. 5. Shaft 32 is both long enough and flexible enough to permit insertion of proximal shaft end 54 through urethra 10 into bladder 12 (FIG. 1). In a preferred embodiment, catheter shaft 32 is extruded from a thermoplastic elastomer. Thermoplastic materials are less expensive than medical-grade silicone, and are capable of being thermally processed, thereby obviating the need for adhesive bonding to the silicone, and the relatively long curing times associated therewith. Multi-lobe balloon 71 is attached to outer surface 52 of shaft 32, preferably by thermal welding or a comparable attachment technique such as adhesive bonding, at one or more points on outer surface 52. Multi-lobe balloon 71 is preferably formed of a thermoplastic film wrapped around shaft 32, such as a polyurethane blown film in an exemplary embodiment. The construction and operation of multi-lobe balloon 71 is described in more detail with respect to FIG. 5.

Figure 3:
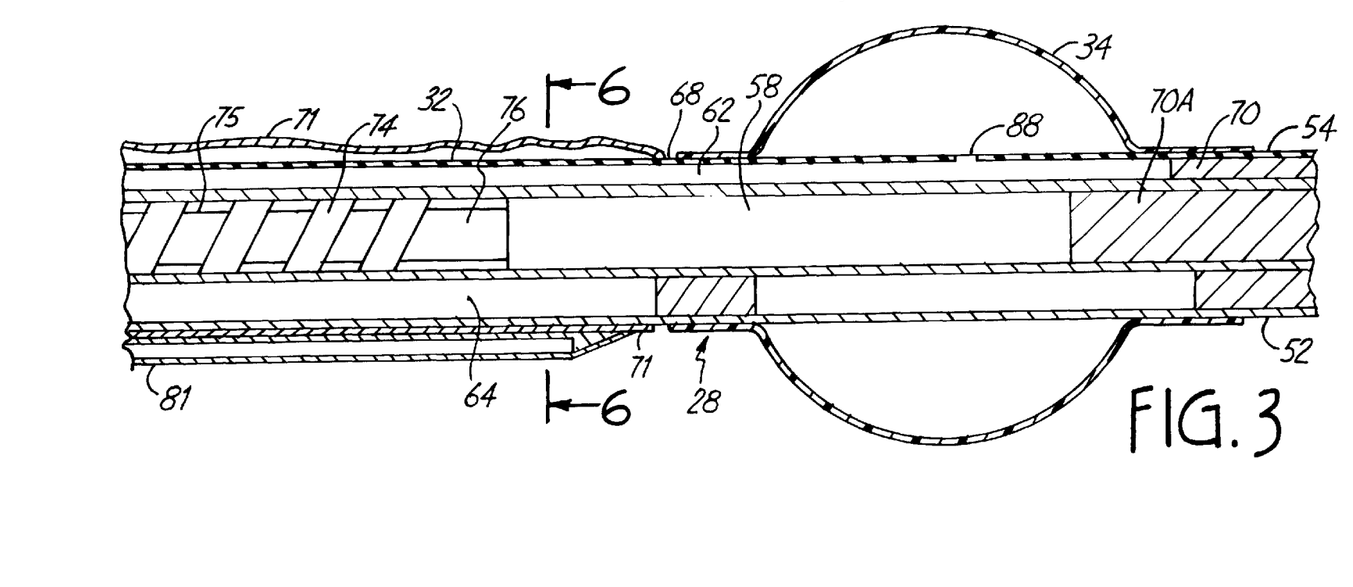
FIG. 3 is a section view of the proximal end of the thermal therapy catheter of the present invention.
Figure 4:
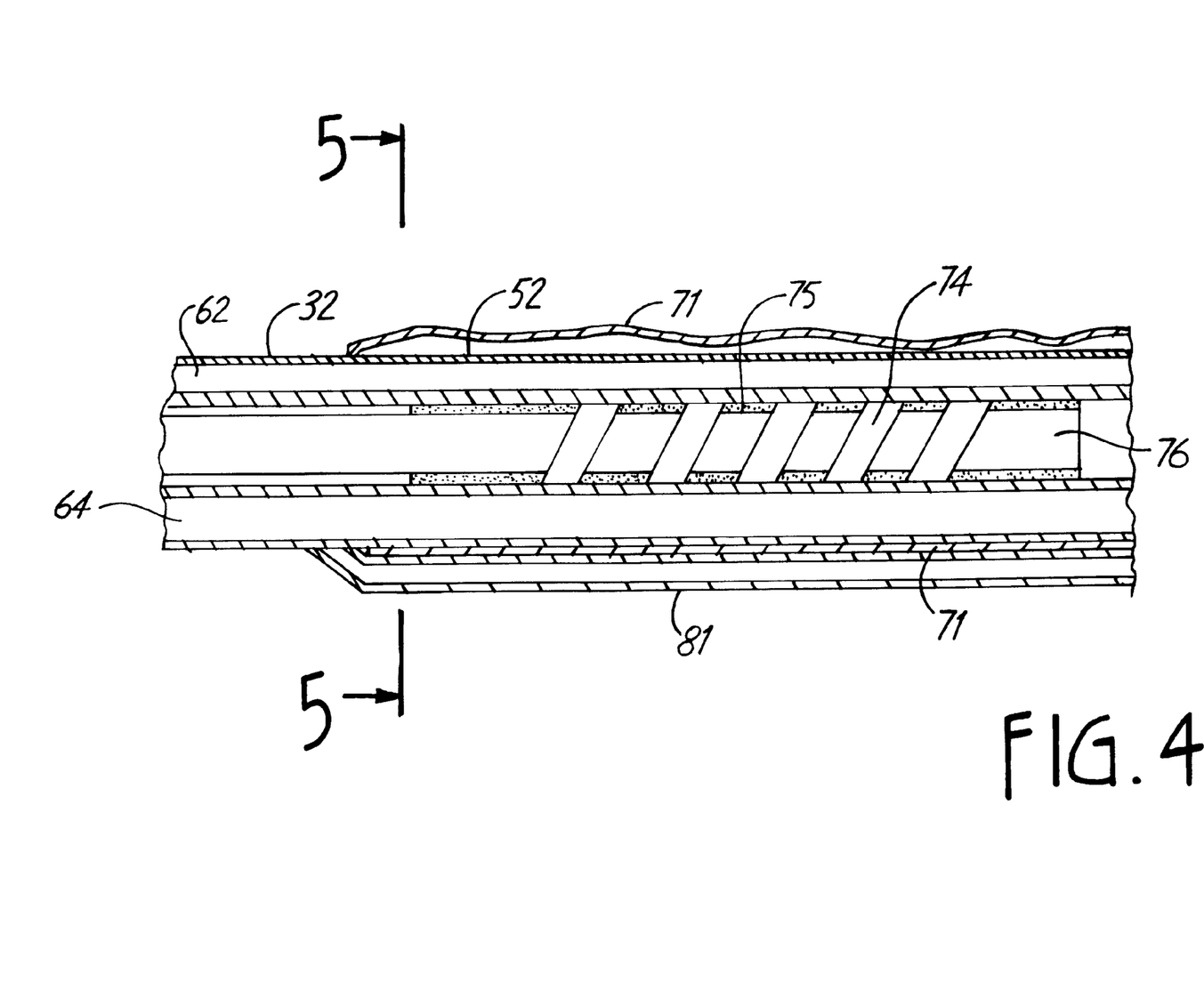
FIG. 4 is a section view of an intermediate portion of the thermal therapy catheter of the present invention.
Figure 6:
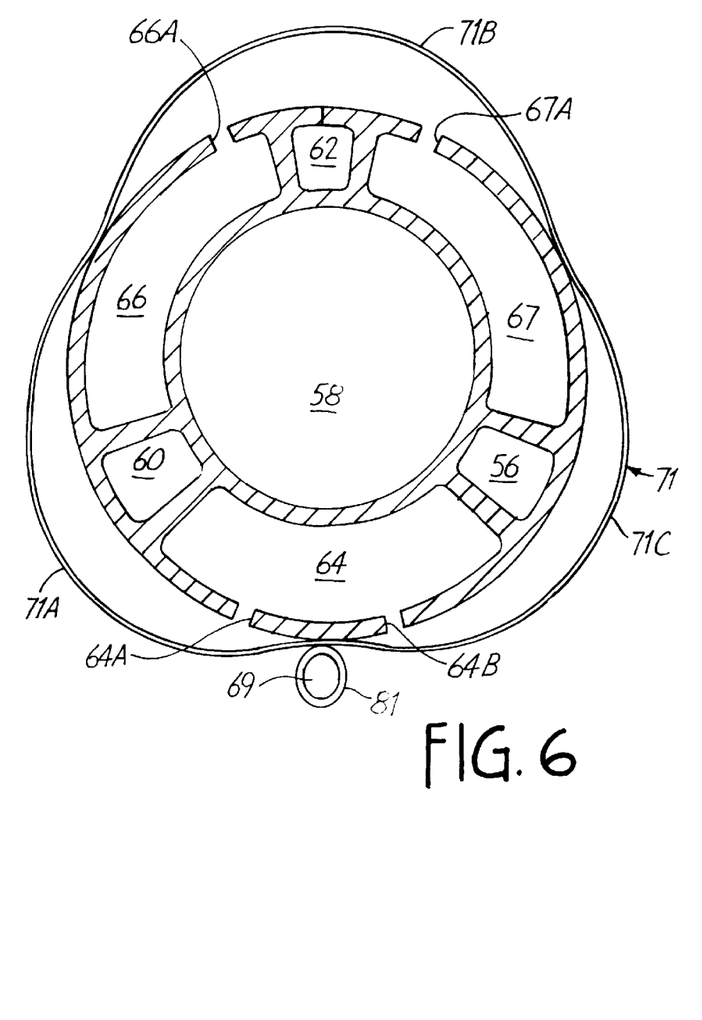
FIG. 6 is a section view of the thermal therapy catheter of the present invention, taken along line 6—6 of FIG. 3.

FIG. 3 is a sectional view of catheter shaft 32 adjacent proximal end 50 of shaft 32, and FIG. 4 is a section view of an intermediate portion of catheter shaft 32. Both FIG. 3 and FIG. 4 illustrate multi-lobe balloon 71 in its deflated state, for insertion of catheter 28 into urethra 10. FIG. 5 is a sectional view of catheter shaft 32 taken along line 5—5 of FIG. 4, and FIG. 6 is a sectional view of catheter shaft 32 taken along line 6—6 of FIG. 3. Both FIG. 5 and FIG. 6 illustrate multi-lobe balloon 71 in its inflated state, for operating to cool the wall of urethra 10 when microwave antenna 74 is energized. As shown in FIGS. 3–6, shaft 32 includes temperature sensing fiber lumen 56, microwave antenna lumen 58, urine drainage lumen 60, balloon inflation lumen 62, cooling fluid intake lumen 64 and cooling fluid exhaust lumens 66 and 67. Lumens 56, 58, 60, 62, 64, 66 and 67 generally extend from distal shaft end 50 to proximal shaft end 54, and are located within catheter shaft 32 so as to form a catheter wall having uniform thickness throughout the cross-section of shaft 32, the catheter wall thickness being about 0.008 inches in an exemplary embodiment. Along the length of shaft 32, temperature sensing fiber lumen 56 communicates through the wall of shaft 32 through a channel formed in the catheter wall to temperature sensing fiber tube 81 attached to outer surface 52 of shaft 32. Temperature sensing fiber lumen 56, temperature sensing fiber tube 81 and the channel therebetween are sized to permit insertion of temperature sensing fiber 69 to monitor the temperature of tissue surrounding shaft 32 when it is inserted into urethra 10. Temperature sensing fiber 69 exits handle 30 through port 44 and is connected through manifold 35 to thermometry unit 39, which calculates temperature based on the optical information provided by temperature sensing fiber 69. Temperature sensing fiber lumen 69 has a generally trapezoidal cross-section, and together with the catheter walls on either side between cooling lumens 64 and 67 has an included angle of about 30.5 degrees.

In an exemplary embodiment, microwave antenna lumen 58 is located eccentric to the longitudinal axis of shaft 32, nearer first side 68 of shaft 32 than second side 72 of shaft 32. In an exemplary embodiment, the center of antenna lumen is offset from the center of shaft 32 towards first side 68 of shaft 32 by 0.007 inches. Antenna lumen 58 is sealed at a proximal end by plug 70A. At its distal end, microwave antenna lumen 58 communicates with microwave antenna port 44. Microwave antenna 74 is permanently positioned within antenna lumen 58 at the proximal end of shaft 32 near balloon 34. Antenna 74 is positioned within antenna lumen 58 so as to be generally situated adjacent the diseased tissue of prostate 14 when shaft 32 is properly positioned in urethra 10. Antenna 74 includes wound coils carried at the proximal end of coaxial cable 76. The distal end of coaxial cable 76 is connected to manifold 35 by a conventional quick-coupling fitting 73. Coaxial cable 76 communicates with microwave generating source 38 by connection cable 76A, which is connected between microwave generating source 38 and manifold 35. In an exemplary embodiment, microwave antenna 74 is an impedance-matched antenna implemented in the manner generally disclosed in U.S. Pat. No. 5,413,588, which has been incorporated herein by reference. It is also preferable for antenna lumen 58 and antenna 74 to have a relatively large radial cross-section, about 0.131 inches in an exemplary embodiment, since a larger antenna radius results in lower transmission line losses and also provides greater column stiffness to facilitate insertion of shaft 32 into urethra 10. More specifically, because microwave antenna lumen 58 is located nearer first side 68 of shaft 32 than second size 72 of shaft 72, the orientation of shaft 32 in urethra 10 must be controlled to achieve the desired preferential heating pattern. Thus, microwave antenna 74 is designed to effectively transmit 100% of the torque applied to handle 30 on to the tip of shaft 32 at proximal end 54; that is, if handle 30 is rotated 20 degrees, the tip of shaft 32 at proximal end 54 also rotates 20 degrees. Microwave generating source 38 produces up to 100 watts of electrical power in an exemplary embodiment, in a frequency range of 902–928 MHz, within the FCC-ISM standard range of frequencies. When antenna 74 is energized by microwave generating source 38, antenna 74 emits electromagnetic energy which causes heating of tissue within prostate 14.

In one preferred embodiment of the thermal therapy catheter of the present invention, a tip design may be used at proximal end 54 of catheter shaft 32 as described in U.S. Pat. No. 5,628,770 entitled DEVICES FOR TRANSURETHRAL THERMAL THERAPY, which is hereby incorporated by reference.

Urine drainage lumen 60 is positioned adjacent antenna lumen 58, between antenna lumen 58 and lobe 71A of multi-lobe balloon 71. Urine drainage lumen 60 has a generally trapezoidal cross-section, and together with the catheter walls on either side between cooling lumens 64 and 66 has an included angle of about 30.5 degrees. Urine drainage lumen 60 communicates with urine drainage port 42 of handle 30 at distal shaft end 50 and defines a drainage path for urine when proximal end 54 of shaft 32 is inserted through urethra 10 into bladder 12. Urine drains from bladder 12 through urine drainage lumen 60 and out urine drainage port 42 when proximal shaft end 54 is inserted within bladder 12. Drainage of urine from bladder 12 is necessary due to frequent bladder spasms which occur during transurethral thermal therapy. Again, as mentioned above, in one preferred embodiment the tip design disclosed in U.S. Pat. No. 5,628,770, which has been incorporated by reference, may be used with catheter 28 of the present invention.

Balloon inflation lumen 62 is positioned adjacent antenna lumen 58, between antenna lumen 58 and lobe 71B of multi-lobe balloon 71. Balloon inflation lumen 62 has a generally trapezoidal cross-section, and together with the catheter walls on either size between cooling lumens 66 and 67 has an included angle of about 29 degrees. Balloon inflation lumen 62 communicates with inflation port 40 of handle 30 to allow inflation fluid to flow in and out of balloon inflation lumen 62, and communicates through aperture 88 to inflate retention balloon 34.

Cooling fluid intake lumen 64 is positioned adjacent to antenna lumen 58, between antenna lumen 58 and temperature sensing fiber tube 81 between lobes 71A and 71C of multi-lobe balloon 71. Cooling fluid intake lumen 64 has a generally arcuate cross-section, and extends from distal end 50 to proximal end 54 of shaft 32. Fluid contained within cooling fluid intake lumen 64 absorbs a portion of the microwave energy emitted by the microwave antenna within antenna lumen 58 to control the volume of prostatic tissue in a selected direction that is heated above 45° C. for a time sufficient to necrose the tissue. Fluid within cooling fluid intake lumen 64 also absorbs a portion of the heat energy generated by microwave energy from adjacent tissues via thermal conduction. In an exemplary embodiment, cooling fluid intake lumen 64 an included angle of about 90 degrees.

Cooling fluid exhaust lumens 66 and 67 are positioned adjacent to antenna lumen 58, with cooling fluid exhaust lumen 66 being located generally between antenna lumen 58 and lobes 71A and 71B of multi-lobe balloon 71 and cooling fluid exhaust lumen 67 being located generally between antenna lumen 58 and lobes 71B and 71C of multi-lobe balloon 71. Cooling fluid exhaust lumens 66 and 67 have a generally arcuate cross-section, and extend from distal end 50 to proximal end 54 of shaft 32. Fluid contained within cooling fluid exhaust lumens 66 and 67 absorbs a portion of the microwave energy emitted by the microwave antenna within antenna lumen 58 to control the volume of prostatic tissue in a selected direction that is heated above 45° C. for a time sufficient to necrose the tissue. Fluid within cooling fluid exhaust lumens 66 and 67 also absorbs a portion of the heat energy generated by microwave energy from adjacent tissues via thermal conduction. In an exemplary embodiment, cooling fluid exhaust lumens 66 and 67 each have an included angle of about 90 degrees.

Cooling fluid intake lumen 64 and exhaust lumens 66 and 67 cooperate with cooling system 36 via ports 46 and 48 of handle 30 to provide a selectively controlled flow of fluid through cooling lumens 64, 66 and 67 during a treatment session. As shown in FIG. 6, at proximal end 54 of shaft 32 cooling lumens 64, 66 and 67 communicate with the interior of multi-lobe balloon 71 so as to provide cooling fluid to inflate multi-lobe balloon 71. Specifically, cooling fluid intake lumen 64 communicates with the interior of lobe 71A through aperture 64A and communicates with the interior of lobe 71C through aperture 64B. Cooling fluid exhaust lumen 66 communicates with the interior of lobe 71B through aperture 66A, and cooling fluid exhaust lumen 67 communicates with the interior of lobe 71B through aperture 67A. Therefore, in operation, cooling fluid flows from cooling system 36 to cooling fluid feed line 94B and on through port 46 of handle 30 into cooling fluid intake lumen 64. The cooling fluid continues to flow under dynamic fluid pressure through apertures 64A and 64B to inflate lobes 71A and 71C of multi-lobe balloon 71, and into a defined fluid flow pathway of multi-lobe balloon 71 through lobes 71A, 71B and 71C (shown in more detail in FIG. 7). Cooling fluid flows from lobe 71B through apertures 66A and 67A into cooling fluid exhaust lumens 66 and 67, and exits shaft 32 at distal end 50 thereof through port 48 of handle 30, and on through cooling fluid return line 96B and manifold 35 to cooling system 36 for re-chilling and recirculation. Cooling fluid feed line 96B and return line 96B are each provided with a conventional quick-coupling fitting 65A and 65B, respectively, which permits catheter 28 to be easily disconnected from cooling system 36. In an exemplary embodiment, the cooling fluid is deionized water provided by cooling system 36, chilled to an appropriate temperature so as to maintain the temperature of tissue immediately surrounding catheter shaft 32 at a predetermined value while power is applied from microwave antenna 74 to heat diseased prostate tissue. A method of controlling coolant temperature and microwave power to maintain a predetermined tissue temperature is disclosed in U.S. application Ser. No. 09/210,033 entitled METHOD OF CONTROLLING THERMAL THERAPY filed Dec. 11, 1998 by E. Rudie, J. Flachman, J. Burgett and T. Larson, which is hereby incorporated by reference. The water is pumped at a rate sufficient to provide dynamic pressure to inflate multi-lobe balloon 71 to create an outer balloon diameter of about 24 French, thereby ensuring excellent wall contact with the urethra and enhancing the efficiency of the conductive cooling performed by the circulating cooling fluid flowing in multi-lobe balloon 71.

Figure 7:
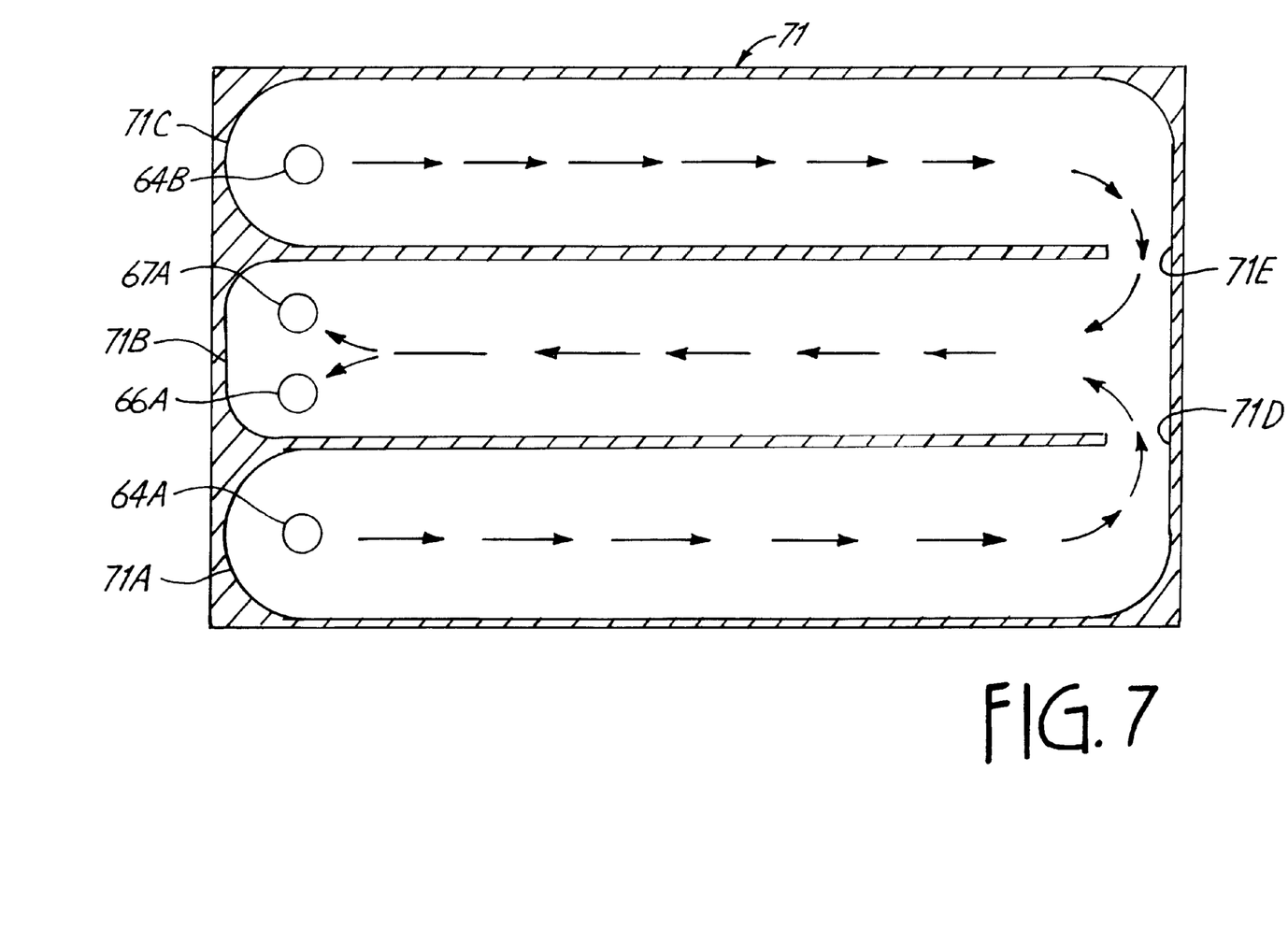
FIG. 7 is a diagram illustrating the flow path of cooling fluid through the multi-lobe balloon of the present invention.

FIG. 7 illustrates the pattern of fluid flow through multi-lobe balloon 71 according to an embodiment of the present invention. For the purpose of illustration, multi-lobe balloon 71 is shown in FIG. 7 as "flattened out" in two dimensions; it should be understood that multi-lobe balloon 71 is wrapped around catheter shaft 32 in a final assembly of the present invention, as shown in the cross-sectional views of FIGS. 5 and 6. The cross-hashed regions of balloon 71 indicate where balloon 71 is thermally welded (or otherwise attached) to the catheter shaft, with the patterns of multi-lobe balloon 71 being formed by heat stamping or an alternative processing method. Cooling fluid is circulated into lobe 71A of multi-lobe balloon 71 through fluid flow aperture 64A and into lobe 71C of multi-lobe balloon 71 through fluid flow aperture 64B. The cooling fluid flows under dynamic pressure in the direction indicated by the arrows, through narrow channels 71D and 71E into lobe 71B of multi-lobe balloon 71, where the fluid exits through fluid flow apertures 66A and 67A into the internal cooling lumens of the catheter. The fluid flow path provided by the present invention ensures that the cooling fluid circulates under sufficient dynamic pressure to inflate multi-lobe balloon 71 to a sufficient diameter to provide consistent wall contact with the urethra, such as about 24 French in an exemplary embodiment. More complex flow patterns in the lobes of balloon 71 are also contemplated by the present invention, which may be realized by heat stamping and thermal welding processes, or alternatively by adhesive bonding processes, to form the appropriate flow pattern. In addition, multi-lobe balloon 71 may be formed with more than the three lobes 71A, 71B and 71C illustrated in FIGS. 5 and 6, thereby forming modifying the fluid flow pattern and inflation characteristics of balloon 71. The actual amount of dynamic fluid flow pressure may be controlled by adjusting a number of parameters, such as the rate at which cooling fluid is pumped from the cooling system, the width of channels 71D and 71E, the size of fluid flow apertures 64A, 64B, 66A and 67A, the width of restricted flow areas elsewhere in the fluid flow path, and other parameters that will be apparent to one skilled in the art. In an exemplary embodiment, dynamic fluid pressure is controlled by an adjustable restrictor located in the fluid flow path proximate to cooling system 36.

The present invention provides an improved thermal therapy catheter designed to enhance the efficiency of treatment of diseased tissue from an adjacent body lumen, particularly for treatment of diseased prostate tissue from a urethrally inserted applicator. A multi-lobe balloon is attached around the catheter shaft, with interiors of the balloon lobes in communication with cooling lumens of the catheter, so that circulation of fluid in the cooling lumens dynamically inflates the balloon lobes. As a result, the balloon lobes come into full contact with the wall of the urethra, and the cooling fluid circulating in the balloon lobes is thereby able to efficiently conduct heat away from the urethral wall tissue to preserve the urethra while delivering microwave energy to heat prostate tissue to high temperatures (above about 45° C.) for a sufficient time to necrose the targeted prostate tissue. Implementing a multi-lobe cooling balloon around the catheter shaft provides a very small wall thickness between the actual cooling fluid and the urethral wall, further enhancing the effects of cooling. In one embodiment, the balloon wall thickness is about 0.002 inches. In addition, the inflatable nature of the multi-lobe cooling balloon allows the catheter to be easily inserted when the balloon is not inflated (with the catheter shaft having a relatively small diameter of about 18 French) while providing the ability to firmly contact the urethral wall to enhance cooling when the balloon is inflated, up to a diameter of about 24 French in one embodiment.

The arrangement and shape of the lumens in the catheter shaft is also designed for efficient operation of the thermal therapy catheter system. As shown in FIGS. 5 and 6, temperature sensing fiber lumen 56, urine drainage lumen 60 and balloon inflation lumen 62 are all formed with generally trapezoidal cross-sections, so as to minimize the included angle of each of these lumens. As a result, the included angle of cooling lumens 64, 66 and 67 is maximized, improving the efficiency of urethral cooling. In addition, lobes 71A, 71B and 71C of multi-lobe balloon 71 are formed with three seams between the respective lobes. Therefore, there is a potential for "hot spots" in the urethral wall at these seams. To allay this potential difficulty, cooling lumens 64, 66 and 67 are specifically designed so as to be located adjacent to those seams, thereby providing sufficient cooling of the urethral wall at the seams of multi-lobe balloon 71 in addition to the inflated lobes of the balloon. Cooling lumens 64, 66 and 67 also extend along the entire length of the microwave antenna to provide internal cooling of the catheter and thereby ensure that the thermoplastic material of the catheter shaft is not melted by the resistive heating produced by the antenna and the heating produced by absorption of microwave energy by the catheter walls.

Temperature sensing fiber 69 within temperature sensing fiber tube 81 is also strategically placed in the catheter design of the present invention. Temperature sensing fiber tube 81 is located in the seam between lobes 71A and 71C of multi-lobe balloon 71, so as to minimize its effect on the outer perimeter shape of the catheter. In addition, the location of temperature sensing fiber tube 81 also ensures that cooling lumen 64 is positioned directly between temperature sensing fiber 69 and the microwave antenna positioned in antenna lumen 58. As a result, the resistive heating produced by the microwave antenna has no appreciable effect on the temperature reading obtained by temperature sensing fiber 69; the only variables that affect the temperature reading are the actual temperature of tissue immediately adjacent temperature sensing fiber tube 81 and the temperature of the cooling fluid circulating through cooling lumen 64. The cooling fluid temperature may be compensated for by the thermometry unit to yield an accurate value for the actual tissue temperature, which is useful information for controlling the thermal therapy procedure.

As a result of the catheter design of the present invention and the efficient cooling of the body lumen wall provided by the invention, a substantial depth of tissue may be heated above about 45° C. for a time sufficient to necrose the tissue, while protecting the body lumen wall from thermal damage. Under the regulation of an effective control algorithm, such as is disclosed in the aforementioned U.S. application Ser. No. 09/210,033, which has been incorporated herein by reference, the catheter design of the present invention is able to necrose substantially the entire prostate while protecting healthy tissues such as the urethral wall and the rectum, with a treatment time of approximately 30 minutes or less and no need for anesthesia. The present invention therefore offers an extremely attractive therapy option for treating tissue disease such as BPH, with excellent long-term results and a low risk of morbidity or other side effects.

It should be understood that while the present invention has been described with respect to selected embodiments, minor modifications may be made to certain details of the catheter designs shown while still practicing the principles and teachings of the present invention. For example, while specific lumen shapes and sizes have been disclosed, other shapes and sizes are contemplated by the present invention, while practicing the teachings of the invention relating to the motivation for relative lumen positioning and the like.

Although the present invention has been described with reference to preferred embodiments, workers skilled in the art will recognize that changes may be made in form and detail without departing from the spirit and scope of the invention.

What is claimed is:

1. A device for treating tissue adjacent to a body lumen, the device comprising:

a catheter shaft having an outer surface, the catheter shaft being insertable into the body lumen;

an energy-emitting element carried by the catheter shaft;

a multi-lobe balloon formed around the outer surface of the catheter shaft at least partially surrounding the energy-emitting element, opposing ends of the multi-lobe balloon being sealingly connected to the catheter shaft to form a chamber between the multi-lobe balloon and the outer surface of the catheter shaft; and means for circulating a fluid between the outer surface of the catheter shaft and the multi-lobe balloon in a defined fluid flow path.

2. The device of claim 1, wherein the means for circulating a fluid between the outer surface of the catheter shaft and the multi-lobe balloon comprises:

at least one fluid intake lumen in the catheter shaft, the at least one fluid intake lumen being in fluid communication with at least one lobe of the multi-lobe balloon;

at least one fluid exhaust lumen in the catheter shaft, the at least one fluid exhaust lumen being in fluid communication with at least one lobe of the multi-lobe balloon; and a cooling system providing fluid to the at least one fluid intake lumen and receiving fluid from the at least one fluid exhaust lumen.

3. The device of claim 2, wherein the multi-lobe balloon comprises three lobes around the outer surface of the catheter shaft and the means for circulating a fluid comprises one fluid intake lumen and two fluid exhaust lumens.

4. The device of claim 3, wherein the fluid intake lumen is located adjacent a first seam between a first lobe and a second lobe of the multi-lobe balloon, a first fluid exhaust lumen is located adjacent a second seam between the first lobe and a third lobe of the multi-lobe balloon, and a second fluid exhaust lumen is located adjacent a third seam between the second lobe and the third lobe of the multi-lobe balloon.

5. The device of claim 4, wherein the fluid intake lumen includes a first fluid flow aperture for communicating fluid with the first lobe of the multi-lobe balloon and a second fluid flow aperture for communicating fluid with the third lobe of the multi-lobe balloon, the first fluid exhaust lumen includes a third fluid flow aperture for communicating fluid with the second lobe of the multi-lobe balloon and the second fluid exhaust lumen includes a fourth fluid flow aperture for communicating fluid with the second lobe of the multi-lobe balloon.

6. The device of claim 1, further comprising:

a temperature sensor fiber lumen in the catheter shaft;

a temperature sensor fiber tube attached to the outer surface of the catheter shaft between lobes of the multi-lobe balloon;

a channel in the catheter shaft connecting the temperature sensor fiber lumen and the temperature sensor fiber tube; and a temperature sensor fiber extending through the temperature sensor fiber lumen, the channel and the temperature sensor fiber tube to sense a temperature of tissue immediately adjacent to the temperature sensor fiber tube.

7. The device of claim 6, wherein the means for circulating a fluid between the outer surface of the catheter shaft and the multi-lobe balloon comprises:

at least one fluid intake lumen in the catheter shaft, the at least one fluid intake lumen being in fluid communication with at least one lobe of the multi-lobe balloon;

at least one fluid exhaust lumen in the catheter shaft, the at least one fluid exhaust lumen being in fluid communication with at least one lobe of the multi-lobe balloon;

a cooling system providing fluid to the at least one fluid intake lumen and receiving fluid from the at least one fluid exhaust lumen; and wherein at least one of the fluid intake lumen and the fluid exhaust lumen is located between the energy-emitting element and the temperature sensor fiber tube attached to the outer surface of the catheter shaft between lobes of the multi-lobe balloon.

8. The device of claim 1, wherein the catheter shaft is insertable into a urethra for treating diseased prostate tissue adjacent the urethra.

9. The device of claim 1, further comprising:

a urine drainage lumen in the catheter shaft.

10. The device of claim 1, further comprising:

a balloon inflation lumen in the catheter shaft; and a retention balloon at an end of the catheter shaft, the retention balloon being in fluid communication with the balloon inflation lumen so as to be inflatable in a bladder to secure the catheter shaft in place in the urethra.

11. A method of treating tissue adjacent to a body lumen, the method comprising:

inserting a catheter shaft into the body lumen;

supplying a fluid to inflate a multi-lobe balloon having opposing ends sealingly attached to the catheter shaft in a defined fluid flow path; and providing microwave energy from a microwave generator to an antenna in the catheter shaft for emission to the tissue adjacent to the body lumen.

12. The method of claim 11, wherein the step of supplying the fluid to inflate the multi-lobe balloon comprises circulating water through cooling lumens in the catheter shaft positioned around the antenna, the cooling lumens being in fluid communication with interior portions of the multi-lobe balloon.

* * * * *